United States Patent
Bence et al.

(10) Patent No.: US 9,603,619 B2
(45) Date of Patent: *Mar. 28, 2017

(54) CUTTING BALLOON CATHETER HAVING FLEXIBLE ATHEROTOMES

(71) Applicant: Boston Scientific Scimed, Inc., Maple Grove, MN (US)

(72) Inventors: Steven W. Bence, Vista, CA (US); Alexander J. Asconeguy, Murrieta, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 118 days.

This patent is subject to a terminal disclaimer.

(21) Appl. No.: 14/671,214

(22) Filed: Mar. 27, 2015

(65) Prior Publication Data
US 2015/0196319 A1  Jul. 16, 2015

Related U.S. Application Data

(63) Continuation of application No. 14/158,982, filed on Jan. 20, 2014, now Pat. No. 9,017,353, which is a continuation of application No. 13/719,391, filed on Dec. 19, 2012, now Pat. No. 8,690,903, which is a continuation of application No. 13/235,822, filed on Sep. 19, 2011, now Pat. No. 8,361,096, which is a
(Continued)

(51) Int. Cl.
*A61B 17/3207* (2006.01)
*A61M 25/10* (2013.01)
*A61B 17/22* (2006.01)

(52) U.S. Cl.
CPC ... *A61B 17/320725* (2013.01); *A61M 25/104* (2013.01); *A61B 2017/22061* (2013.01); *A61B 2017/320733* (2013.01)

(58) Field of Classification Search
CPC ........ A61B 17/3207; A61B 17/320725; A61B 2017/22061; A61B 2017/320733; A61M 25/104
See application file for complete search history.

(56) References Cited

U.S. PATENT DOCUMENTS

| 291,170 A | 1/1884 | Edmunds, Jr. |
| 414,350 A | 11/1889 | Warner |
| 508,746 A | 11/1893 | Pease |
(Continued)

FOREIGN PATENT DOCUMENTS

| DE | 3400416 A1 | 7/1985 |
| DE | 3402573 A1 | 8/1985 |
(Continued)

OTHER PUBLICATIONS

Banning G. et al., "A Method for Creating a Coronary-Myocardial Artery," Surgery, Jun. 1966, vol. 59, No. 6, pp. 1061-1064.
(Continued)

*Primary Examiner* — Ryan J Severson
(74) *Attorney, Agent, or Firm* — Seager, Tufte & Wickhem LLP

(57) ABSTRACT

A cutting balloon catheter and method of making and using the same. The cutting balloon catheter may include a catheter shaft having a balloon coupled thereto. One or more cutting members or blades may be coupled to the balloon. The cutting members may configured to be more flexible.

19 Claims, 7 Drawing Sheets

Related U.S. Application Data continuation of application No. 10/987,618, filed on Nov. 12, 2004, now Pat. No. 8,038,691.

(56) References Cited

U.S. PATENT DOCUMENTS

| | | |
|---|---|---|
| 565,799 A | 8/1896 | Rtjmford |
| 784,966 A | 3/1905 | Smith |
| 792,656 A | 6/1905 | Heberling |
| 1,547,328 A | 7/1925 | Jagenberg |
| 2,816,552 A | 12/1957 | Hoffman |
| 3,174,851 A | 3/1965 | Buchler |
| 3,351,463 A | 11/1967 | Buehler |
| 3,400,416 A | 9/1968 | Nicholson et al. |
| 3,402,573 A | 9/1968 | Eide |
| 3,519,626 A | 7/1970 | Beachem et al. |
| 3,635,223 A | 1/1972 | Klieman |
| 3,749,085 A | 7/1973 | Willson et al. |
| 3,753,700 A | 8/1973 | Harrison et al. |
| 3,990,453 A | 11/1976 | Douvas |
| 4,140,126 A | 2/1979 | Choudhury |
| 4,141,364 A | 2/1979 | Schultze |
| 4,263,236 A | 4/1981 | Briggs et al. |
| 4,273,128 A | 6/1981 | Lary et al. |
| 4,292,974 A | 10/1981 | Fogarty et al. |
| 4,406,656 A | 9/1983 | Hattler et al. |
| 4,465,072 A | 8/1984 | Taheri |
| 4,490,421 A | 12/1984 | Levy |
| 4,572,186 A | 2/1986 | Gould et al. |
| 4,574,781 A | 3/1986 | Chin |
| 4,608,984 A | 9/1986 | Fogarty et al. |
| 4,627,436 A | 12/1986 | Leckrone et al. |
| 4,669,469 A | 6/1987 | Gifford et al. |
| 4,685,458 A | 8/1987 | Leckrone |
| 4,686,982 A | 8/1987 | Nash |
| 4,696,667 A | 9/1987 | Masch et al. |
| 4,705,517 A | 11/1987 | DiPisa, Jr. |
| 4,723,549 A | 2/1988 | Wholey et al. |
| 4,728,319 A | 3/1988 | Masch |
| 4,747,405 A | 5/1988 | Leckrone |
| 4,748,982 A | 6/1988 | Horzewski et al. |
| 4,781,186 A | 11/1988 | Simpson et al. |
| 4,784,636 A | 11/1988 | Rydell |
| 4,787,388 A | 11/1988 | Hofmann |
| 4,790,813 A | 12/1988 | Kensey |
| 4,793,348 A | 12/1988 | Palmaz |
| 4,796,629 A | 1/1989 | Grayzel et al. |
| 4,799,479 A | 1/1989 | Spears |
| 4,867,157 A | 9/1989 | McGurk-Burleson et al. |
| 4,886,061 A | 12/1989 | Fischell et al. |
| 4,887,613 A | 12/1989 | Farr et al. |
| 4,896,669 A | 1/1990 | Bhate et al. |
| 4,909,781 A | 3/1990 | Husted |
| 4,921,483 A | 5/1990 | Wijay et al. |
| 4,921,484 A | 5/1990 | Hillstead |
| 4,936,845 A | 6/1990 | Stevens et al. |
| 4,960,410 A | 10/1990 | Pinchuk |
| 4,963,313 A | 10/1990 | Noddin |
| 4,966,604 A | 10/1990 | Reiss |
| 4,979,951 A | 12/1990 | Simpson |
| 4,986,807 A | 1/1991 | Farr |
| 4,994,018 A | 2/1991 | Saper |
| 5,009,659 A | 4/1991 | Hamlin et al. |
| 5,015,231 A | 5/1991 | Keith et al. |
| 5,030,201 A | 7/1991 | Palestrant |
| 5,041,125 A | 8/1991 | Montano, Jr. |
| 5,042,985 A | 8/1991 | Elliott et al. |
| 5,047,040 A | 9/1991 | Simpson et al. |
| 5,053,007 A | 10/1991 | Euteneuer |
| 5,053,044 A | 10/1991 | Mueller et al. |
| 5,071,424 A | 12/1991 | Reger et al. |
| 5,074,841 A | 12/1991 | Ademovic et al. |
| 5,074,871 A | 12/1991 | Groshong et al. |
| 5,078,722 A | 1/1992 | Stevens |
| 5,078,725 A | 1/1992 | Enderle et al. |
| 5,084,010 A | 1/1992 | Plaia et al. |
| 5,085,662 A | 2/1992 | Willard et al. |
| 5,087,265 A | 2/1992 | Summers et al. |
| 5,100,424 A | 3/1992 | Jang et al. |
| 5,100,425 A | 3/1992 | Fischell et al. |
| 5,102,390 A | 4/1992 | Crittenden et al. |
| 5,102,403 A | 4/1992 | Alt et al. |
| 5,116,318 A | 5/1992 | Hillstead |
| 5,135,482 A | 8/1992 | Neracher et al. |
| 5,147,302 A | 9/1992 | Euteneuer et al. |
| 5,152,773 A | 10/1992 | Redha et al. |
| 5,156,594 A | 10/1992 | Keith et al. |
| 5,156,610 A | 10/1992 | Reger et al. |
| 5,158,564 A | 10/1992 | Schnepp-Pesch |
| 5,176,693 A | 1/1993 | Pannek |
| 5,178,625 A | 1/1993 | Groshong et al. |
| 5,180,368 A | 1/1993 | Garrison et al. |
| 5,181,920 A | 1/1993 | Mueller et al. |
| 5,192,291 A | 3/1993 | Pannek |
| 5,196,024 A | 3/1993 | Barath et al. |
| 5,196,025 A | 3/1993 | Ranalletta et al. |
| 5,209,749 A | 5/1993 | Buelna |
| 5,209,799 A | 5/1993 | Vigil |
| 5,224,945 A | 7/1993 | Pannek |
| 5,226,430 A | 7/1993 | Spears et al. |
| 5,226,887 A | 7/1993 | Farr et al. |
| 5,226,909 A | 7/1993 | Evans et al. |
| 5,242,396 A | 9/1993 | Evard et al. |
| 5,248,311 A | 9/1993 | Black et al. |
| 5,250,059 A | 10/1993 | Andreas et al. |
| 5,295,959 A | 3/1994 | Gurbel et al. |
| 5,300,025 A | 4/1994 | Wantink et al. |
| 5,312,425 A | 5/1994 | Evans et al. |
| 5,318,576 A | 6/1994 | Plassche et al. |
| 5,320,634 A | 6/1994 | Vigil et al. |
| 5,328,472 A | 7/1994 | Steinke et al. |
| 5,336,234 A | 8/1994 | Vigil et al. |
| 5,342,301 A | 8/1994 | Saab et al. |
| 5,342,307 A | 8/1994 | Euteneuer et al. |
| 5,346,505 A | 9/1994 | Leopold et al. |
| 5,350,361 A | 9/1994 | Tsukashima et al. |
| 5,372,601 A | 12/1994 | Lary et al. |
| 5,395,361 A | 3/1995 | Fox et al. |
| 5,399,164 A | 3/1995 | Snoke et al. |
| 5,403,334 A | 4/1995 | Evans et al. |
| 5,409,454 A | 4/1995 | Fischell et al. |
| 5,411,466 A | 5/1995 | Hess |
| 5,411,478 A | 5/1995 | Stillabower et al. |
| 5,415,654 A | 5/1995 | Daikuzono et al. |
| 5,417,653 A | 5/1995 | Sahota et al. |
| 5,417,703 A | 5/1995 | Brown et al. |
| 5,423,745 A | 6/1995 | Todd et al. |
| 5,425,711 A | 6/1995 | Ressemann et al. |
| 5,425,712 A | 6/1995 | Goodin |
| 5,437,659 A | 8/1995 | Leckrone et al. |
| 5,441,510 A | 8/1995 | Simpson et al. |
| 5,449,343 A | 9/1995 | Samson et al. |
| 5,456,666 A | 10/1995 | Campbell et al. |
| 5,456,681 A | 10/1995 | Hajjar et al. |
| 5,458,572 A | 10/1995 | Campbell et al. |
| 5,478,319 A | 12/1995 | Campbell et al. |
| 5,487,730 A | 1/1996 | Marcadis et al. |
| 5,496,308 A | 3/1996 | Brown et al. |
| 5,507,760 A | 4/1996 | Wynne et al. |
| 5,507,761 A | 4/1996 | Duer et al. |
| 5,522,818 A | 6/1996 | Keith et al. |
| 5,522,825 A | 6/1996 | Kropf et al. |
| 5,538,510 A | 7/1996 | Fontirroche et al. |
| 5,542,924 A | 8/1996 | Snoke et al. |
| 5,549,556 A | 8/1996 | Ndondo-Lay et al. |
| 5,554,121 A | 9/1996 | Ainsworth et al. |
| 5,556,405 A | 9/1996 | Lary |
| 5,556,408 A | 9/1996 | Farhat |
| 5,569,277 A | 10/1996 | Evans et al. |
| 5,571,087 A | 11/1996 | Ressemann et al. |
| 5,616,149 A | 4/1997 | Barath et al. |
| 5,628,761 A | 5/1997 | Rizik et al. |
| 5,643,209 A | 7/1997 | Fugoso et al. |
| 5,643,296 A | 7/1997 | Hundertmark et al. |
| 5,649,941 A | 7/1997 | Lary et al. |

(56) References Cited

U.S. PATENT DOCUMENTS

| | | | |
|---|---|---|---|
| 5,662,671 A | 9/1997 | Barbut et al. | |
| 5,669,920 A | 9/1997 | Conley et al. | |
| 5,681,336 A | 10/1997 | Clement et al. | |
| 5,697,944 A | 12/1997 | Lary et al. | |
| 5,713,913 A | 2/1998 | Lary et al. | |
| 5,718,684 A | 2/1998 | Gupta | |
| 5,720,724 A | 2/1998 | Ressemann et al. | |
| 5,728,123 A | 3/1998 | Lemelson et al. | |
| 5,743,875 A | 4/1998 | Sirhan et al. | |
| 5,759,191 A | 6/1998 | Barbere | |
| 5,769,819 A | 6/1998 | Schwab et al. | |
| 5,769,865 A | 6/1998 | Kermode et al. | |
| 5,792,158 A | 8/1998 | Lary et al. | |
| 5,797,935 A | 8/1998 | Barath et al. | |
| 5,800,450 A | 9/1998 | Lary et al. | |
| 5,820,594 A | 10/1998 | Fontirroche et al. | |
| 5,824,173 A | 10/1998 | Fontirroche et al. | |
| 5,827,201 A | 10/1998 | Samson et al. | |
| 5,827,225 A | 10/1998 | Ma Schwab | |
| 5,827,310 A | 10/1998 | Marin et al. | |
| 5,895,402 A | 4/1999 | Hundertmark et al. | |
| 5,921,958 A | 7/1999 | Ressemann et al. | |
| 5,931,819 A | 8/1999 | Fariabi | |
| 5,993,469 A | 11/1999 | McKenzie et al. | |
| 5,997,557 A | 12/1999 | Barbut et al. | |
| 6,010,521 A | 1/2000 | Lee et al. | |
| 6,024,722 A | 2/2000 | Rau et al. | |
| 6,030,371 A | 2/2000 | Pursley et al. | |
| 6,039,699 A | 3/2000 | Viera | |
| 6,066,149 A | 5/2000 | Samson et al. | |
| 6,068,623 A | 5/2000 | Zadno-Azizi et al. | |
| 6,110,192 A | 8/2000 | Ravenscroft et al. | |
| 6,117,153 A | 9/2000 | Lary et al. | |
| 6,139,510 A | 10/2000 | Palermo et al. | |
| 6,142,975 A | 11/2000 | Jalisi et al. | |
| 6,165,140 A | 12/2000 | Ferrera et al. | |
| 6,165,167 A | 12/2000 | Delaloye | |
| 6,165,292 A | 12/2000 | Abrams et al. | |
| 6,168,571 B1 | 1/2001 | Solar et al. | |
| 6,179,851 B1 | 1/2001 | Barbut et al. | |
| 6,190,332 B1 | 2/2001 | Muni et al. | |
| 6,193,686 B1 | 2/2001 | Estrada et al. | |
| 6,197,013 B1* | 3/2001 | Reed | A61F 2/86 604/103.02 |
| 6,213,957 B1 | 4/2001 | Milliman et al. | |
| 6,217,549 B1 | 4/2001 | Selmon et al. | |
| 6,217,567 B1 | 4/2001 | Zadno-Azizi et al. | |
| 6,221,006 B1 | 4/2001 | Dubrul et al. | |
| 6,241,690 B1 | 6/2001 | Burkett et al. | |
| 6,254,550 B1 | 7/2001 | McNamara et al. | |
| 6,258,108 B1 | 7/2001 | Lary | |
| 6,283,743 B1 | 9/2001 | Traxler et al. | |
| 6,306,105 B1 | 10/2001 | Rooney et al. | |
| 6,306,151 B1 | 10/2001 | Lary | |
| 6,309,399 B1 | 10/2001 | Barbut et al. | |
| 6,319,242 B1 | 11/2001 | Patterson et al. | |
| 6,344,029 B1 | 2/2002 | Estrada et al. | |
| 6,355,016 B1 | 3/2002 | Bagaoisan et al. | |
| 6,383,146 B1 | 5/2002 | Klint et al. | |
| 6,387,075 B1 | 5/2002 | Stivland et al. | |
| 6,394,995 B1 | 5/2002 | Solar et al. | |
| 6,398,798 B2 | 6/2002 | Selmon et al. | |
| 6,409,863 B1 | 6/2002 | Williams et al. | |
| 6,425,882 B1 | 7/2002 | Vigil | |
| 6,428,552 B1 | 8/2002 | Sparks | |
| 6,471,673 B1 | 10/2002 | Kastenhofer | |
| 6,471,713 B1 | 10/2002 | Vargas et al. | |
| 6,533,754 B1 | 3/2003 | Hisamatsu et al. | |
| 6,544,276 B1 | 4/2003 | Azizi | |
| 6,562,062 B2 | 5/2003 | Jenusaitis et al. | |
| 6,602,265 B2 | 8/2003 | Dubrul et al. | |
| 6,632,231 B2 | 10/2003 | Radisch, Jr. | |
| 6,730,105 B2 | 5/2004 | Shiber | |
| 6,942,680 B2* | 9/2005 | Grayzel | A61F 2/958 606/159 |
| 6,951,566 B2* | 10/2005 | Lary | A61B 17/320725 606/159 |
| 6,991,617 B2* | 1/2006 | Hektner | A61M 25/104 604/103.01 |
| 7,011,670 B2* | 3/2006 | Radisch, Jr. | A61B 17/320725 606/159 |
| 7,070,576 B2* | 7/2006 | O'Brien | A61B 17/320725 604/96.01 |
| 7,153,315 B2* | 12/2006 | Miller | A61B 17/320725 606/159 |
| 7,172,609 B2* | 2/2007 | Radisch, Jr. | A61B 17/320725 606/159 |
| 7,186,237 B2* | 3/2007 | Meyer | A61M 25/104 604/96.01 |
| 7,270,673 B2* | 9/2007 | Yee | A61B 17/320725 606/159 |
| 7,279,002 B2* | 10/2007 | Shaw | A61B 17/22 606/159 |
| 7,291,158 B2 | 11/2007 | Crow et al. | |
| 7,338,463 B2* | 3/2008 | Vigil | A61B 17/320725 604/22 |
| 7,413,558 B2* | 8/2008 | Kelley | A61B 17/320725 604/103.07 |
| 7,494,497 B2* | 2/2009 | Weber | A61B 17/320725 606/159 |
| 7,517,352 B2* | 4/2009 | Evans | A61B 17/22 606/167 |
| 7,566,319 B2 | 7/2009 | McAuley et al. | |
| 7,662,163 B2* | 2/2010 | Grayzel | A61F 2/958 606/159 |
| 7,754,047 B2 | 7/2010 | Kelley | |
| 7,758,604 B2* | 7/2010 | Wu | A61B 17/320725 606/108 |
| 7,771,447 B2* | 8/2010 | Kunis | A61B 17/22 604/103.14 |
| 7,780,626 B2* | 8/2010 | Wu | A61B 17/320725 604/523 |
| 7,799,043 B2* | 9/2010 | O'Brien | A61B 17/320725 606/159 |
| 7,883,537 B2* | 2/2011 | Grayzel | A61F 2/958 606/159 |
| 7,887,557 B2* | 2/2011 | Kelley | A61B 17/320725 604/96.01 |
| 7,985,234 B2* | 7/2011 | Wang | A61B 17/320725 606/159 |
| 7,993,358 B2* | 8/2011 | O'Brien | A61B 17/320725 604/103.08 |
| 8,038,691 B2 | 10/2011 | Bence et al. | |
| 8,043,259 B2* | 10/2011 | Radisch, Jr. | A61B 17/320725 427/2.1 |
| 8,048,093 B2* | 11/2011 | Mapes | A61B 17/320725 606/159 |
| 8,211,354 B2* | 7/2012 | Burton | A61B 17/320725 264/532 |
| 8,361,096 B2 | 1/2013 | Bence et al. | |
| 8,491,615 B2* | 7/2013 | Manderfeld | A61B 17/320725 606/159 |
| 8,523,887 B2* | 9/2013 | Grayzel | A61F 2/958 606/159 |
| 8,690,903 B2* | 4/2014 | Bence | A61B 17/320725 606/159 |
| 9,017,353 B2* | 4/2015 | Bence | A61B 17/320725 606/159 |
| 2002/0010489 A1 | 1/2002 | Grayzel et al. | |
| 2002/0029015 A1* | 3/2002 | Camenzind | A61B 17/22 604/97.02 |
| 2002/0029052 A1* | 3/2002 | Evans | A61B 17/22 606/159 |
| 2002/0082592 A1 | 6/2002 | Lary | |
| 2003/0032973 A1 | 2/2003 | Jenusaitis et al. | |
| 2003/0040770 A1 | 2/2003 | Radisch, Jr. | |
| 2003/0144677 A1 | 7/2003 | Lary | |
| 2003/0144683 A1* | 7/2003 | Sirhan | A61B 17/320725 606/194 |
| 2003/0153870 A1* | 8/2003 | Meyer | A61M 25/104 604/96.01 |

(56) References Cited

U.S. PATENT DOCUMENTS

| | | | |
|---|---|---|---|
| 2003/0163148 A1 | 8/2003 | Wang et al. | |
| 2003/0229370 A1* | 12/2003 | Miller | A61B 17/320725 606/159 |
| 2004/0034384 A1 | 2/2004 | Fukaya | |
| 2004/0064093 A1* | 4/2004 | Hektner | A61M 25/104 604/103.01 |
| 2004/0098014 A1* | 5/2004 | Flugelman | A61B 17/320725 606/192 |
| 2004/0098018 A1* | 5/2004 | Radisch, Jr. | A61B 17/320725 606/194 |
| 2004/0122457 A1 | 6/2004 | Weber | |
| 2004/0127920 A1 | 7/2004 | Radisch, Jr. | |
| 2004/0133223 A1 | 7/2004 | Weber | |
| 2004/0230178 A1 | 11/2004 | Wu | |
| 2004/0243156 A1 | 12/2004 | Wu et al. | |
| 2005/0033225 A1* | 2/2005 | Wu | A61B 17/320725 604/96.01 |
| 2005/0038383 A1* | 2/2005 | Kelley | A61B 17/320725 604/103.06 |
| 2005/0102020 A1* | 5/2005 | Grayzel | A61F 2/958 623/1.11 |
| 2005/0119678 A1* | 6/2005 | O'Brien | A61B 17/320725 606/159 |
| 2005/0137615 A1* | 6/2005 | Mapes | A61B 17/320725 606/159 |
| 2005/0137616 A1* | 6/2005 | Vigil | A61B 17/320725 606/170 |
| 2005/0137617 A1* | 6/2005 | Kelley | A61B 17/320725 606/170 |
| 2005/0137618 A1* | 6/2005 | Kunis | A61B 17/22 606/192 |
| 2005/0149082 A1* | 7/2005 | Yee | A61B 17/320725 606/159 |
| 2005/0228343 A1* | 10/2005 | Kelley | A61B 17/320725 604/96.01 |
| 2005/0240148 A1 | 10/2005 | Cheves et al. | |
| 2005/0245864 A1* | 11/2005 | O'Brien | A61B 17/320725 604/96.01 |
| 2005/0261721 A1* | 11/2005 | Radisch | A61B 17/320725 606/192 |
| 2006/0015133 A1* | 1/2006 | Grayzel | A61F 2/958 606/192 |
| 2006/0106412 A1* | 5/2006 | Crow | A61B 17/320725 606/192 |
| 2006/0106413 A1* | 5/2006 | Bence | A61B 17/320725 606/192 |
| 2006/0184191 A1* | 8/2006 | O'Brien | A61B 17/320725 606/192 |
| 2009/0192537 A1* | 7/2009 | O'Brien | A61B 17/320725 606/159 |
| 2010/0274271 A1* | 10/2010 | Kelley | A61B 17/320725 606/159 |
| 2010/0312264 A1* | 12/2010 | O'Brien | A61B 17/320725 606/159 |
| 2011/0077677 A1* | 3/2011 | Grayzel | A61F 2/958 606/191 |
| 2011/0213401 A1* | 9/2011 | Grayzel | A61F 2/958 606/192 |
| 2011/0288479 A1* | 11/2011 | Burton | A61B 17/320725 604/103.08 |
| 2012/0016403 A1* | 1/2012 | Bence | A61B 17/320725 606/192 |
| 2012/0172901 A1* | 7/2012 | Manderfeld | A61B 17/320725 606/159 |
| 2012/0253281 A1* | 10/2012 | Burton | A61B 17/320725 604/101.01 |
| 2013/0018396 A1* | 1/2013 | Gunderson | A61B 17/320725 606/159 |
| 2013/0110142 A1* | 5/2013 | Bence | A61B 17/320725 606/159 |
| 2013/0284352 A1* | 10/2013 | Manderfeld | A61B 17/320725 156/245 |
| 2014/0128895 A1* | 5/2014 | Bence | A61B 17/320725 606/159 |
| 2015/0196319 A1* | 7/2015 | Bence | A61B 17/320725 606/159 |

FOREIGN PATENT DOCUMENTS

| | | |
|---|---|---|
| DE | 3519626 A1 | 12/1986 |
| EP | 291170 A1 | 11/1988 |
| EP | 414350 B1 | 8/1994 |
| EP | 565799 B1 | 8/1996 |
| EP | 784966 B1 | 1/2003 |
| EP | 732656 B1 | 7/2003 |
| GB | 1547328 A | 6/1979 |
| WO | 9007909 A1 | 7/1990 |
| WO | 9117714 A1 | 11/1991 |

OTHER PUBLICATIONS

Lary, Banning G., "A Method to Create and Correct Stenosis of a Coronary Artery," Archives of Surgery, Nov. 1966, vol. 93, pp. 828-830.

Lary, Banning A, "A Epicardial Purse String Suture for Closing Coronary Arteriotomy," The American Surgeon, Mar. 1967, vol. 33, No. 3, pp. 213-214.

Lary, Banning G., "Coronary Artery Incision and Dilation," Archives of Surgery, Dec. 1980, vol. 115, pp. 1478-1480.

Lary, Banning G., "Coronary Artery Resection and Replacement by a Blood Conduit," Surgery, Apr. 1969, vol. 65, No. 4, pp. 584-589.

Lary, Banning G., "Effect of Endocardial Incisions on Myocardial Blood Flow," Archives of Surgery, Sep. 1963, vol. 87, pp. 424-427.

Lary, B.G., "Experimental Maintenance of Life by Intravenous Oxygen, Preliminary Report," Clinical Congress of the American College of Surgeons, San Francisco, Nov. 5-9, 1951, pp. 30-35.

Lary, Banning G., et al., "Experimental Vein Angioplasty of the Circumflex Coronary Artery," Journal of Surgical Research, Sep. 1974, vol. 17, No. 3, pp. 210-214.

Lary, Banning G., "Method for Increasing the Diameter of Long Segments of the Coronary Artery," The American Surgeon, Jan. 1966, vol. 32, No. 1, pp. 33-35.

Lary, Banning G., et al., "Myocardial Revascularization Experiments Using the Epicardium," Archives of Surgery, Jan. 1969, vol. 98, pp. 69-72.

Lary, Banning G., "Onlay Vein Graft for the Correction of Coronary Artery Obstruction," Surgery, Apr. 1966, vol. 59, No. 4, pp. 547-551.

Lary, Banning G., "Surgery for Coronary Artery Disease," Nursing Clinics of North America, Sep. 1967, vol. 2, No. 3, pp. 537-542.

Lary, Banning G., et al., "The 'Coronary Myocardial Artery' for Coronary Artery Disease," Diseases of the Chest, Apr. 1996, vol. 49, No. 4, pp. 412-419.

* cited by examiner ated Oct. 18, 2011, the entire disclosure of which is incorporated herein by reference.

CUTTING BALLOON CATHETER HAVING FLEXIBLE ATHEROTOMES

CROSS-REFERENCE TO RELATED APPLICATIONS

This application is a continuation of U.S. patent application Ser. No. 14/158,982, filed on Jan. 20, 2014, which is a continuation of U.S. patent application Ser. No. 13/719,391, filed on Dec. 19, 2012, now U.S. Pat. No. 8,690,903, issued Apr. 8, 2014, which is a continuation of U.S. patent application Ser. No. 13/235,822, filed on Sep. 19, 2011, now U.S. Pat. No. 8,361,096, issued Jan. 29, 2013, which is a continuation of U.S. patent application Ser. No. 10/987,618, filed on Nov. 12, 2004, now U.S. Pat. No. 8,038,691, issued Oct. 18, 2011, the entire disclosure of which is incorporated herein by reference.

FIELD OF THE INVENTION

The present invention pertains to angioplasty and angioplasty balloon catheters. More particularly, the present invention pertains to angioplasty balloon catheters that include one or more cutting edges coupled to the angioplasty balloon.

BACKGROUND

Heart and vascular disease are major problems in the United States and throughout the world. Conditions such as atherosclerosis result in blood vessels becoming blocked or narrowed. This blockage can result in lack of oxygenation of the heart, which has significant consequences since the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire so that the balloon is positioned adjacent a stenotic lesion. The balloon is then inflated, and the restriction of the vessel is opened.

One of the major obstacles in treating coronary artery disease and/or treating blocked blood vessels is re-stenosis. Evidence has shown that cutting the stenosis, for example, with an angioplasty balloon equipped with a cutting blade, during treatment can reduce incidence of re-stenosis. Additionally, cutting the stenosis may reduce trauma at the treatment site and/or may reduce the trauma to adjacent healthy tissue. Cutting blades may also be beneficial additions to angioplasty procedures when the targeted occlusion is hardened or calcified. It is believed typical angioplasty balloons, alone, may not be able to expand certain of these hardened lesions. Thus, angioplasty balloons equipped with cutting edges have been developed to attempt to enhance angioplasty treatments. There is an ongoing need for improved angioplasty devices, including cutting angioplasty balloons, and improved methods of treating intravascular stenoses and occlusions.

BRIEF SUMMARY

The present invention relates to angioplasty balloon catheters. In at least some embodiments, an example balloon catheter may include a catheter shaft having a balloon coupled thereto. One or more cutting members or blades may be coupled to the balloon. The cutting members may be configured to be more flexible. These and other features are described in more detail below.

DETAILED DESCRIPTION

Figure 1:
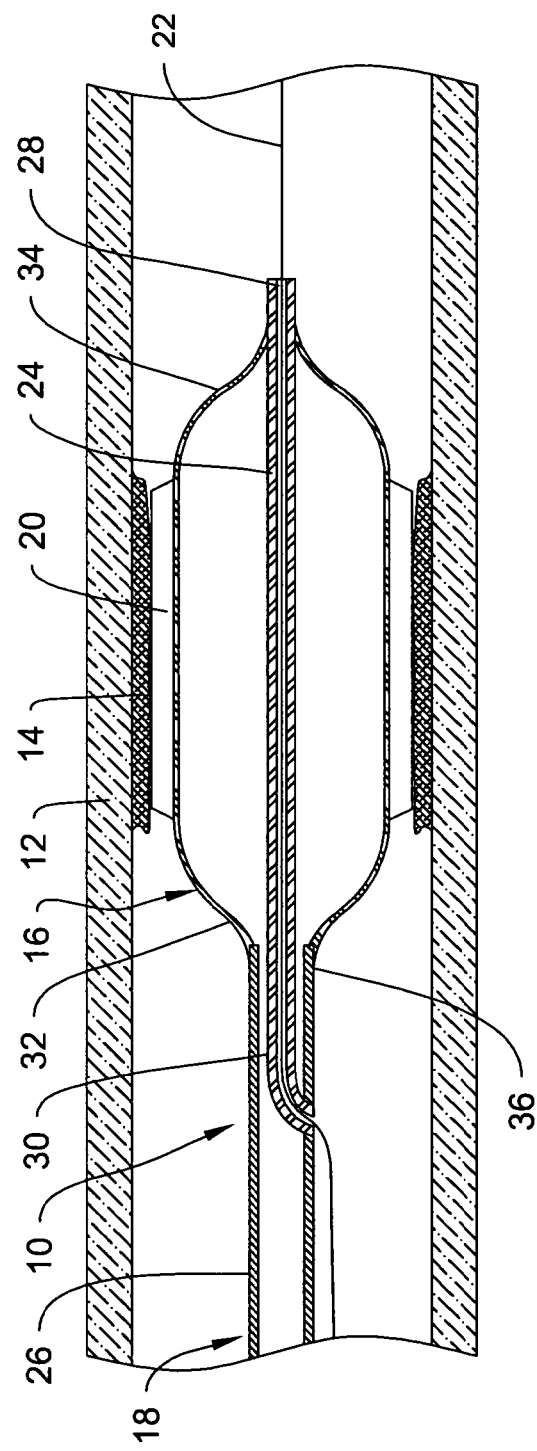
FIG. 1 is a partial cross-sectional side view of an example cutting balloon catheter disposed in a blood vessel.

The following description should be read with reference to the drawings wherein like reference numerals indicate like elements throughout the several views. The detailed description and drawings illustrate example embodiments of the claimed invention.

FIG. 1 is a partial cross-sectional side view of an example catheter 10 disposed in a blood vessel 12 and positioned adjacent an intravascular lesion 14. Catheter 10 may include a balloon 16 coupled to a catheter shaft 18. One or more cutting members or blades 20 may be coupled to balloon 16. In general, catheter 10 may be advanced over a guidewire 22, through the vasculature, to a target area. Balloon 16 can then be inflated to expand lesion 14, and cutting members 20 may cut lesion 14. The target area may be within any suitable peripheral or cardiac vessel lumen location.

Cutting members 20 may vary in number, position, and arrangement about balloon 16. For example, catheter 10 may include one, two, three, four, five, six, or more cutting members 20 that are disposed at any position along balloon 16 and in a regular, irregular, or any other suitable pattern. In general, cutting members 20 may be configured to have enhanced flexibility. Increasing the flexibility of cutting members 20 may desirably impact a number of characteristics and features of catheter 10. For example, increasing the flexibility may improve the tracking ability and general deliverability of catheter 10 through the often tortuous anatomy. Additionally, increasing the flexibility may allow catheter 10 to be navigable to a larger number of intravascular locations, including some that may not be readily reachable by other, less flexible, cutting balloon catheters. In general, the enhanced flexibility is the result of a structural feature of cutting members 20 or a structural modification to cutting members 20 or other components of catheter 10 that increases the flexibility of cutting members 20. Some examples of these features and modifications are described in more detail below.

Balloon 16 may be made from typical angioplasty balloon materials including polymers such as polyethylene terephthalate (PET), polyetherimid (PEI), polyethylene (PE), etc. Some other examples of suitable polymers, including lubricious polymers, may include polytetrafluoroethylene (PTFE), ethylene tetrafluoroethylene (ETFE), fluorinated ethylene propylene (FEP), polyoxymethylene (POM), polybutylene terephthalate (PBT), polyether block ester, polyurethane, polypropylene (PP), polyvinylchloride (PVC), polyether-ester (for example, a polyether-ester elastomer such as ARNITEL® available from DSM Engineering Plastics), polyester (for example, a polyester elastomer such as HYTREL® available from DuPont), polyamide (for example, DURETHAN® available from Bayer or CRISTAMID® available from Elf Atochem), elastomeric polyamides, block polyamide/ethers, polyether block amide (PEBA, for example, available under the trade name PEBAX®), silicones, Marlex high-density polyethylene, Marlex low-density polyethylene, linear low density polyethylene (for example, REXELL®), polyetheretherketone (PEEK), polyimide (PI), polyphenylene sulfide (PPS), polyphenylene oxide (PPO), polysulfone, nylon, perfluoro(propyl vinyl ether) (PFA), other suitable materials, or mixtures, combinations, copolymers thereof, polymer/metal composites, and the like. In some embodiments, it may be desirable to use high modulus or generally stiffer materials so as to reduce balloon elongation. The above list of materials includes some examples of higher modulus materials. Some other examples of stiffer materials include polymers blended with liquid crystal polymer (LCP) as well as the materials listed above. For example, the mixture can contain up to about 5% LCP.

Balloon 16 may be configured so that it includes one or more "wings" or wing-shaped regions when balloon 16 is deflated. These wings may appear as a plurality of alternating inward and outward radial deflections in balloon 16 when balloon 16 is deflated. These wings may be desirable for a number of reasons. For example, by including balloon 16 with wings, balloon 16 may have more predictable and consistent re-folding characteristics. Additionally, the wings may be configured so that cutting members 20 can be positioned at the inward-most positions of the deflated balloon 16. This arrangement allows cutting members 20 to be positioned more closely to shaft 18 when balloon 16 is deflated. Accordingly, cutting members 20 can be moved away from the vessel walls where they might otherwise result in contact and, possibly, damage to healthy tissue during movement of catheter 10 within a body lumen. Additionally, alternating the wings and cutting members 20 as well as positioning cutting members 20 relatively close to shaft 18 may allow the wings to fold over and cover cutting members 20 when balloon 16 is deflated. Again, this feature may reduce the exposure of cutting members 20 to the blood vessel.

Shaft 18 may be a catheter shaft, similar to typical catheter shafts. For example, shaft 18 may include an inner tubular member 24 and outer tubular member 26. Tubular members 24/26 may be manufactured from a number of different materials. For example, tubular members 24/26 may be made of metals, metal alloys, polymers, metal-polymer composites or any other suitable materials. Some examples of suitable metals and metal alloys include stainless steel, such as 300 series stainless steel (including 304V, 304 L, and 316 L; 400 series martensitic stainless steel; tool steel; nickel-titanium alloy such as linear-elastic or super-elastic Nitinol, nickel-chromium alloy, nickel-chromium-iron alloy, cobalt alloy, tungsten or tungsten alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), hastelloy, monel 400, inconel 825, or the like; or other suitable material. Some examples of suitable polymers include those described above in relation to balloon 16. Of course, any other polymer or other suitable material including ceramics may be used without departing from the spirit of the invention. The materials used to manufacture inner tubular member 24 may be the same as or be different from the materials used to manufacture outer tubular member 26. Those materials listed herein may also be used for manufacturing other components of catheter 10 including cutting members 20.

Tubular members 24/26 may be arranged in any appropriate way. For example, in some embodiments inner tubular member 24 can be disposed coaxially within outer tubular member 26. According to these embodiments, inner and outer tubular members 24/26 may or may not be secured to one another along the general longitudinal axis of shaft 18. Alternatively, inner tubular member 24 may follow the inner wall or otherwise be disposed adjacent the inner wall of outer tubular member 26. Again, inner and outer tubular members 24/26 may or may not be secured to one another. For example, inner and outer tubular members 24/26 may be bonded, welded (including tack welding or any other welding technique), or otherwise secured at a bond point. In some embodiments, the bond point may be generally disposed near the distal end of shaft 18. However, one or more bond points may be disposed at any position along shaft 18. The bond may desirably impact, for example, the stability and the ability of tubular members 24/26 to maintain their position relative to one another. In still other embodiments, inner and outer tubular member 24/26 may be adjacent to and substantially parallel to one another so that they are non-overlapping. In these embodiments, shaft 18 may include an outer sheath that is disposed over tubular members 24/26.

Inner tubular member 24 may include an inner lumen 28. In at least some embodiments, inner lumen 28 is a guidewire lumen. Accordingly, catheter 10 can be advanced over guidewire 22 to the desired location. The guidewire lumen may extend along essentially the entire length of catheter shaft 18 so that catheter 10 resembles traditional "over-the-wire" catheters. Alternatively, the guidewire lumen may extend along only a portion of shaft 18 so that catheter 10 resembles "single-operator-exchange" or "rapid-exchange" catheters. Regardless of which type of catheter is contemplated, catheter 10 may be configured so that balloon 16 is disposed over at least a region of inner lumen 28. In at least some of these embodiments, inner lumen 28 (i.e., the portion of inner lumen 28 that balloon 16 is disposed over) may be substantially coaxial with balloon 16.

Shaft 18 may also include an inflation lumen 30 that may be used, for example, to transport inflation media to and from balloon 16. The location and position of inflation lumen 30 may vary, depending on the configuration of tubular members 24/26. For example, when outer tubular member 26 is disposed over inner tubular member 24, inflation lumen 30 may be defined within the space between tubular members 24/26. Moreover, depending on the position of inner tubular member 24 within outer tubular member 26, the shape of lumen 30 (i.e., the shape adjacent shaft 18) may vary. For example, if inner tubular member 24 is attached to or disposed adjacent to the inside surface of outer tubular member 26, then inflation lumen 30 may be generally half-moon in shape; whereas if inner tubular member 24 is generally coaxial with outer tubular member 26, then inflation lumen 30 may be generally ring-shaped or annular in shape. It can be appreciated that if outer tubular member 26 is disposed alongside inner tubular member 24, then lumen 30 may be the lumen of outer tubular member 26 or it may be the space defined between the outer surface of tubular members 24/26 and the outer sheath disposed thereover.

Balloon 16 may be coupled to catheter shaft 18 in any of a number of suitable ways. For example, balloon 16 may be adhesively or thermally bonded to shaft 18. In some embodiments, a proximal waist 32 of balloon 16 may be bonded to shaft 18, for example, at outer tubular member 26, and a distal waist 34 may be bonded to shaft 18, for example, at inner tubular member 24. The exact bonding positions, however, may vary. It can be appreciated that a section of proximal waist 32 may not have sections 36 extending therefrom in order for suitable bonding between balloon 16 and outer tubular member 30.

In addition to some of the structures described above, shaft 18 may also include a number of other structural elements, including those typically associated with catheter shafts. For example, shaft 18 may include a radiopaque marker coupled thereto that may aid a user in determining the location of catheter 10 within the vasculature. In addition, catheter 10 may include a folding spring (not shown) coupled to balloon 16, for example, adjacent proximal waist 32, which may further help in balloon folding and refolding. A description of a suitable folding spring can be found in U.S. Pat. No. 6,425,882, which is incorporated herein by reference.

Figure 2:
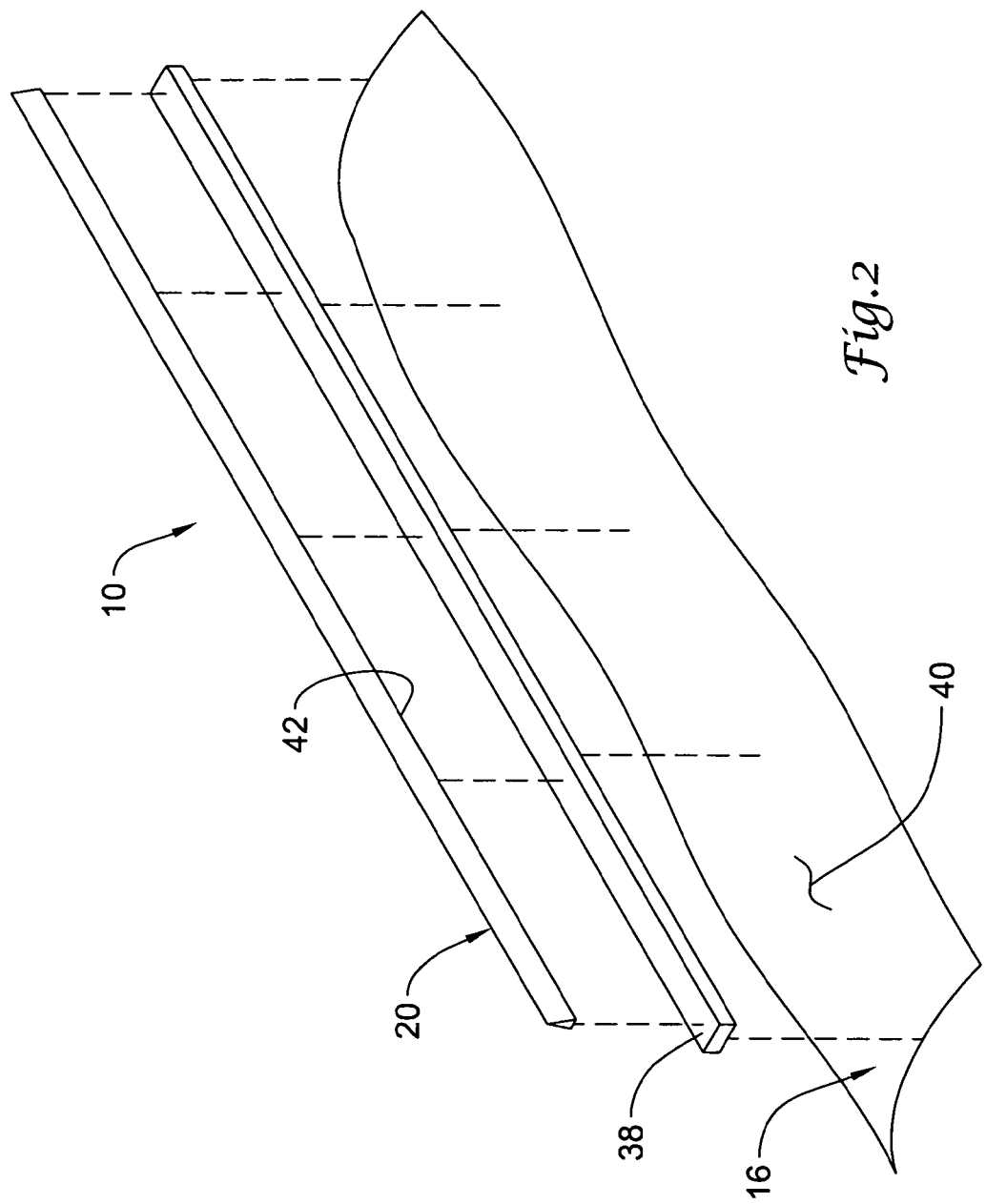
FIG. 2 is a partial perspective view of a cutting member and joining member for connecting the cutting member to a balloon in a manner that allows the cutting member to have greater flexibility.

As described above, cutting members 20 may be configured to have increased flexibility. Increasing the flexibility of cutting members 20 may occur in a number of different manners. For example, a flexible joining member 38 may be coupled to cutting member 20 and to balloon 16 as shown in FIG. 2 (and depicted in an exploded view). Joining member 38 may be formed from a generally flexible or soft material that allows the interface between cutting member 20 and balloon 16 to be somewhat elastic or pliable. For example, joining member 38 may be manufactured from a low durometer polyurethane or any other suitable material (including any of the polymers and other materials disclosed herein). Accordingly, cutting member 20 may be able to move laterally about eight degrees or less. In addition, different portions of cutting member 20 may be able to bend or flex, while other portions remain essentially unchanged.

In at least some embodiments, joining member 38 can be attached to and disposed between cutting member 20 and balloon 16. For example, joining member 38 can be attached to an outer surface 40 of balloon 16 and to a base 42 of the cutting member 20. The attachment of joining member 38 with cutting member 20 and balloon 16 may be achieved in any appropriate manner, such as by adhesive bonding, casting, thermal bonding, mechanically connecting, welding, brazing, and the like, or in any other suitable way. The attachment means need not be the same for the attachment between cutting member 20 and joining member 38 as the means used to attach balloon 16 and joining member 38.

Figure 3:
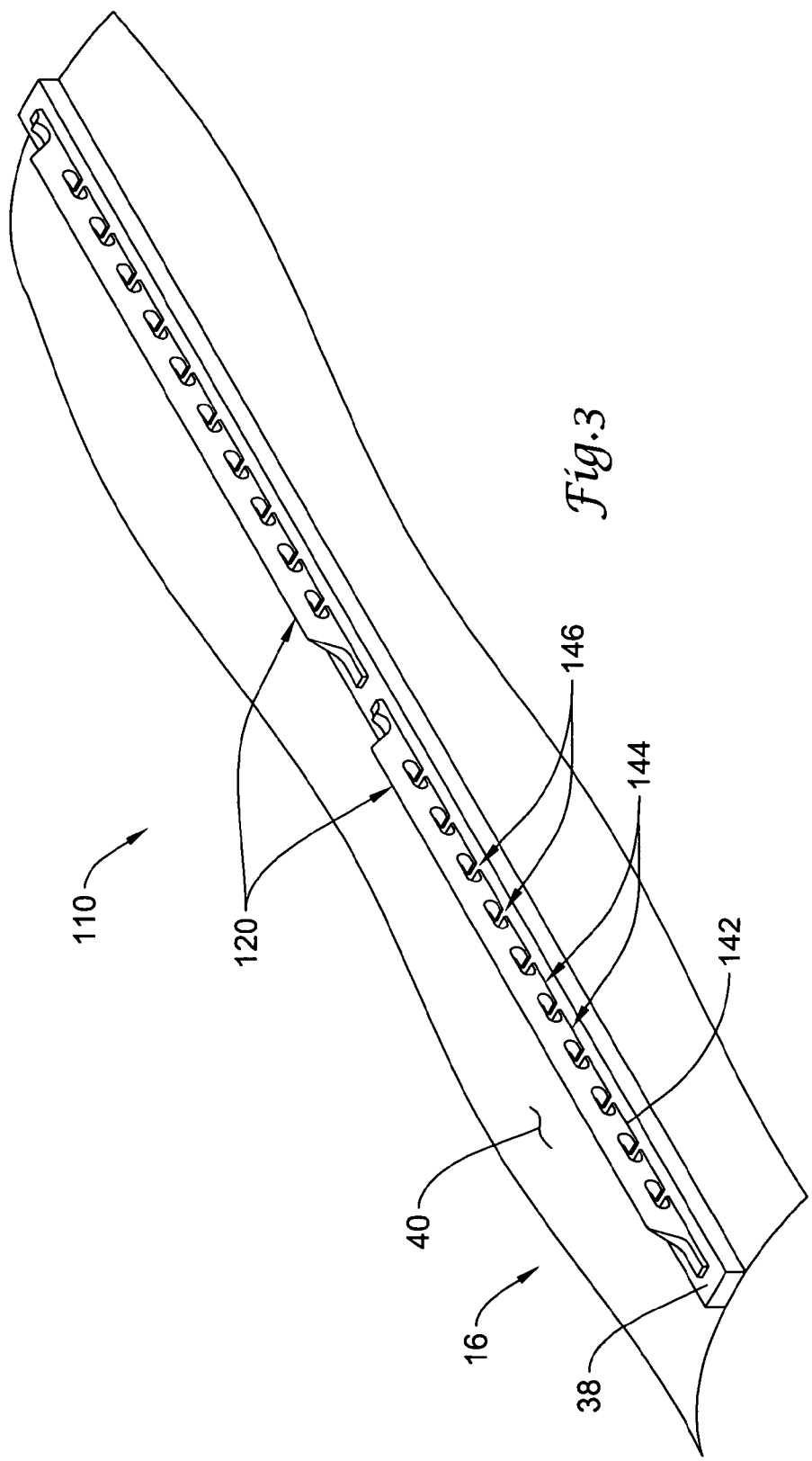
FIG. 3 is a perspective view of a portion of another example cutting balloon catheter, showing an alternative arrangement for enhancing the flexibility of the cutting members.

FIG. 3 depicts a partial perspective view of another catheter 110 that is similar to catheter 10. Catheter 110 includes cutting members 120 that are disposed about balloon 16 in pairs that are arranged in tandem. This embodiment may increase the flexibility of cutting members 120 by dividing what might otherwise be a single cutting blade into multiple parts or segments. Thus, the segmented cutting members 120, by virtue of their shortened length, are more amenable to bending or flexing. In addition, the flexibility of cutting members 120 may be increased by including joining member 38. It can be appreciated that the precise arrangement of cutting members 120 is not intended to be limited to being in tandem. For example, pairs of cutting members 120 may have an arrangement that is longitudinally offset. Moreover, catheter 110 is not intended to be limited to just pairs of cutting members 120, as any suitable number of cutting members 120 may be used without departing from the spirit of the invention.

It can also be seen in FIG. 3 that cutting members 120 may also include a series of alternating tabs 144 and holes or openings 146 that are disposed along the base 142 of cutting members 120. Tabs 144 and openings 146 may have a number of functions. For example, openings 146 (or, more precisely, the portions of cutting member 120 adjacent openings) may provide a location for adhesive (e.g., polyurethane or any other suitable material) to flow into so as to improve the bonding of cutting member 120 with balloon 16. This bonding media may encapsulate the base 142 of cutting member 120. In addition, tabs 144 and openings 146 may also desirably impact the flexibility of cutting member 120. The shape, size, and number of tabs 144 and opening 146 may vary. For example, tabs 144 may have a shape similar to an inverted T (when viewed from the side) or otherwise have a splayed pillar-like shape, and openings 146 may be somewhat rounded or oval. It can be appreciated, however, that tabs 144 and openings 146 are not intended to be limited to these or any other particular shape. Additionally, the size and number of tabs 144 and openings 146 may also vary, typically in relation to the length of cutting members 120. For example, openings 146 may have a height in the range of about 0.002 to about 0.010 inches or so and a width in the range of about 0.007 to about 0.015 inches or so.

Figure 4:
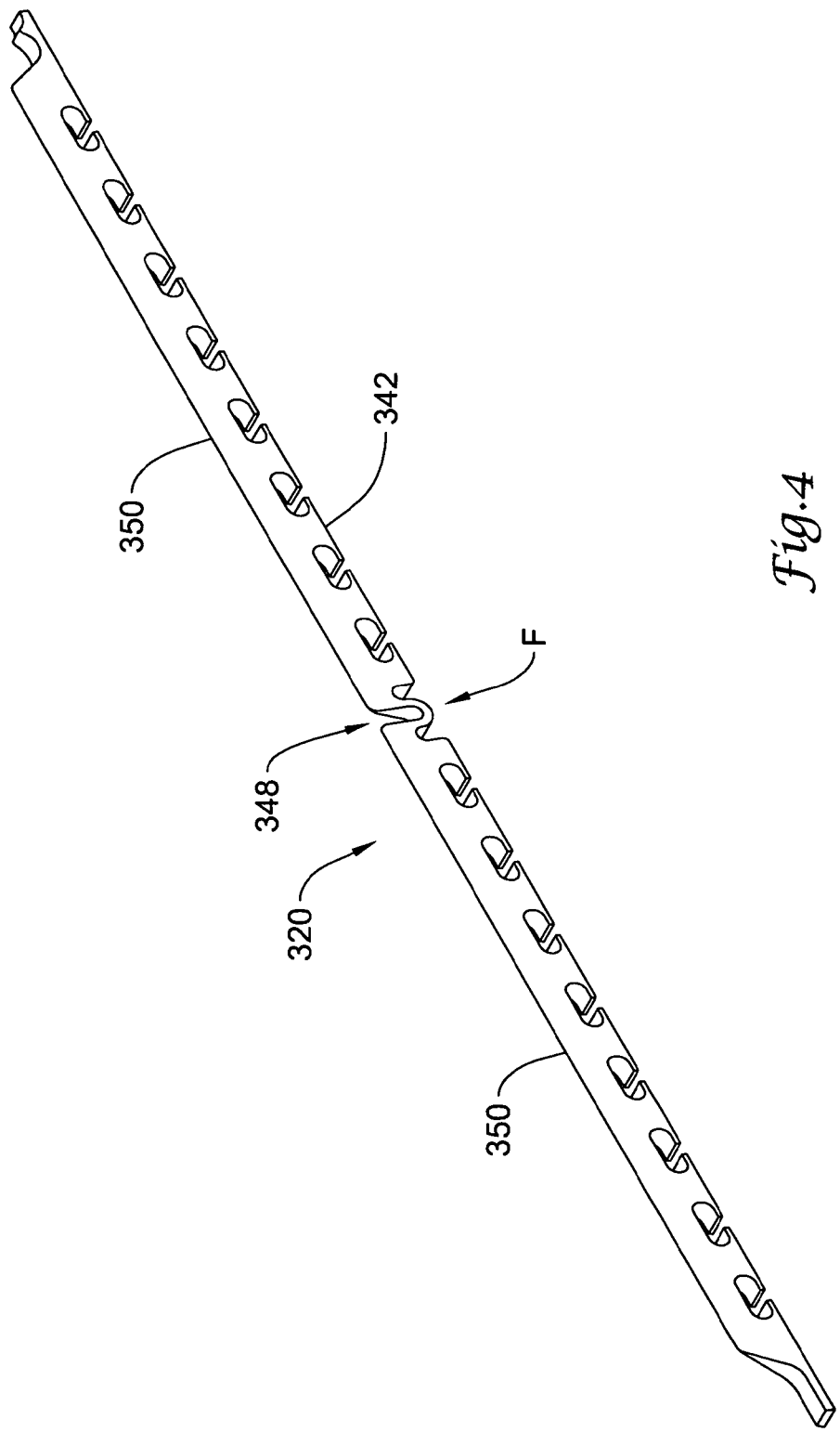
FIG. 4 is a perspective view of another example cutting member.

FIG. 4 illustrates another example cutting member 320 that can be used with any of the catheter embodiments disclosed herein or any other suitable balloon catheter device, including those with joining member 38. Cutting member 320 is similar to any of the other cutting members disclosed herein except that a slot 348 is formed along or adjacent the cutting edge 350.

By including slot 348, cutting member 320 may have increased flexibility by defining a region that is thinned or narrowed. Additionally, because slot 348 is formed in cutting member 320 it can be appreciated that slot 348 creates an increase in flexibility that is localized within the cutting member 320 itself. This feature may be desirable for a number of reasons. For example, because the increase in flexibility is localized within cutting member 320, the desired flexibility characteristics can be incorporated into essentially any cutting balloon catheter by simply substituting cutting member 320 for the cutting blade used on the existing balloon catheter.

Figure 5:
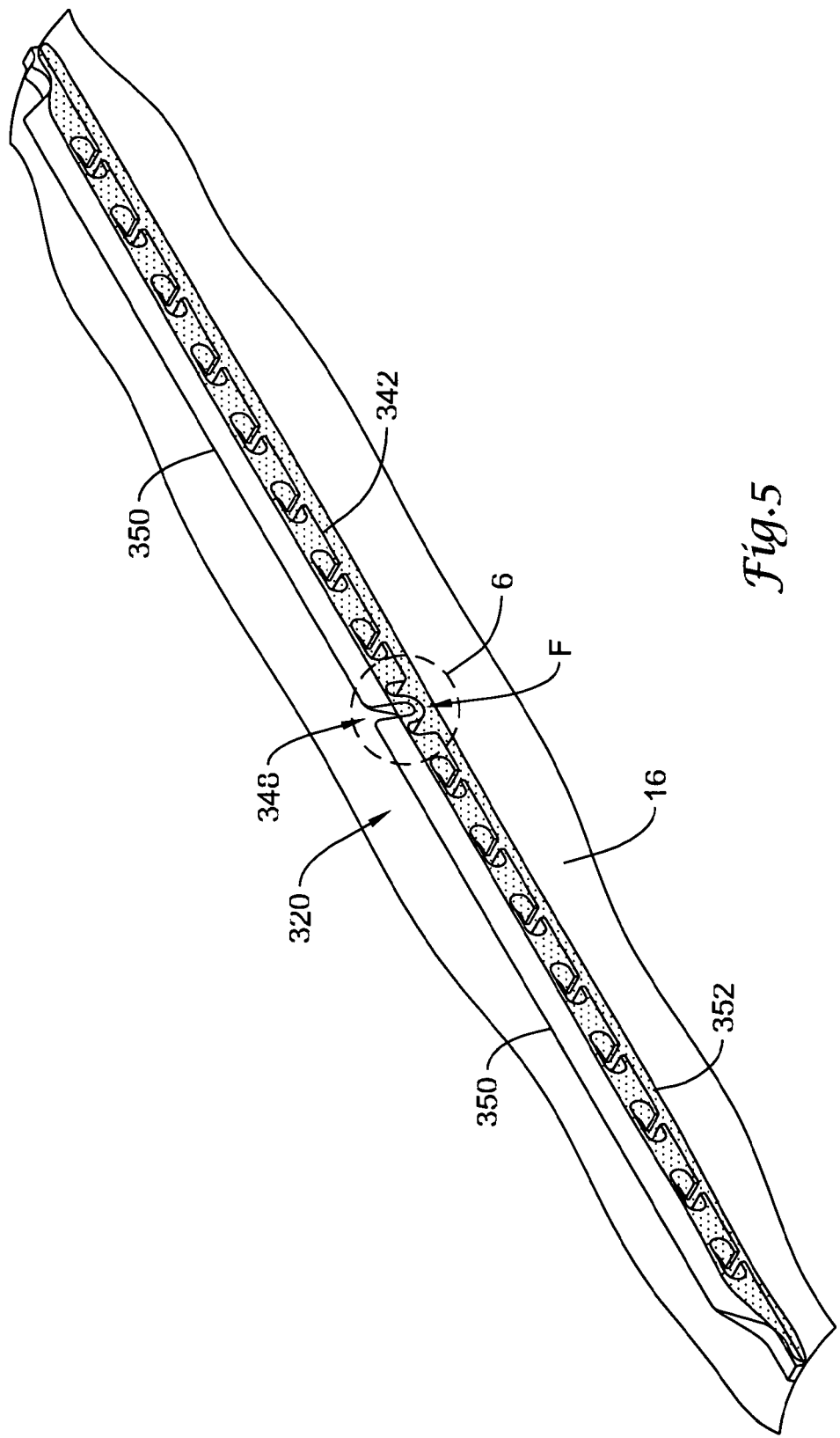
FIG. 5 is a cutaway perspective view of a portion of the cutting member shown in FIG. 4 attached to a balloon.

Another desirable feature of slot 348 is that slot 348 may cause a flex point F of cutting member 320 to be located at or near the bottom or base 342 of cutting member 320. In some embodiments, base 342 may be fully encapsulated within polyurethane or another suitable adhesive or transition material 352 as shown in FIG. 5. Transition material 352 may be made from any suitable material (including those disclosed herein) and may function as an attachment means for attaching cutting member 320 to balloon 16. In some embodiments, transition material 352 may be joining member 38 or any other suitable structure, while in other embodiments, transition material 352 may be used alone or in combination with joining member 38.

Figure 6:
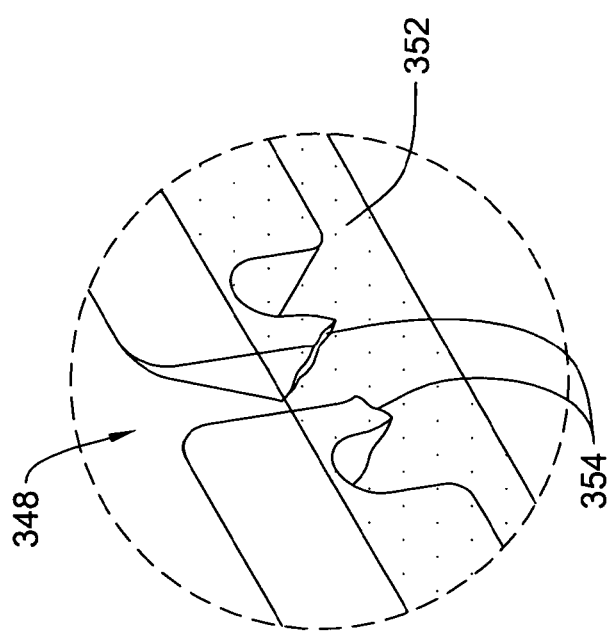
FIG. 6 is an enlarged view of a portion of the cutting member attached to the balloon as shown in FIG. 5, but where the cutting member is broken at a selected location.

Breaks that might occur within cutting member 320 during use or delivery can be isolated at the bottom of the flex point F and, thus, the bottom of cutting member 320. Therefore, transition material 352 at the base 342 of cutting member 320 can surround the broken segments 354 of cutting member 320 and shield balloon 16, other portions of the catheter, and surrounding tissue from unintentional damage as shown in FIG. 6. It can be appreciated that if cutting member 320 were to break, the flexibility of the broken cutting member 320 would be greater than when intact. Thus, the shielding feature provided by encapsulating broken segments 354 in a polyurethane transition material 352 at base 342 of cutting member may be utilized by the clinician to further enhance the flexibility of cutting member 320. For example, the clinician may be able to intentionally break cutting member 320 in order to increase flexibility to an even greater extent, while maintaining confidence that broken segments 354 of cutting member 320 are properly contained and shielded.

Figure 7:
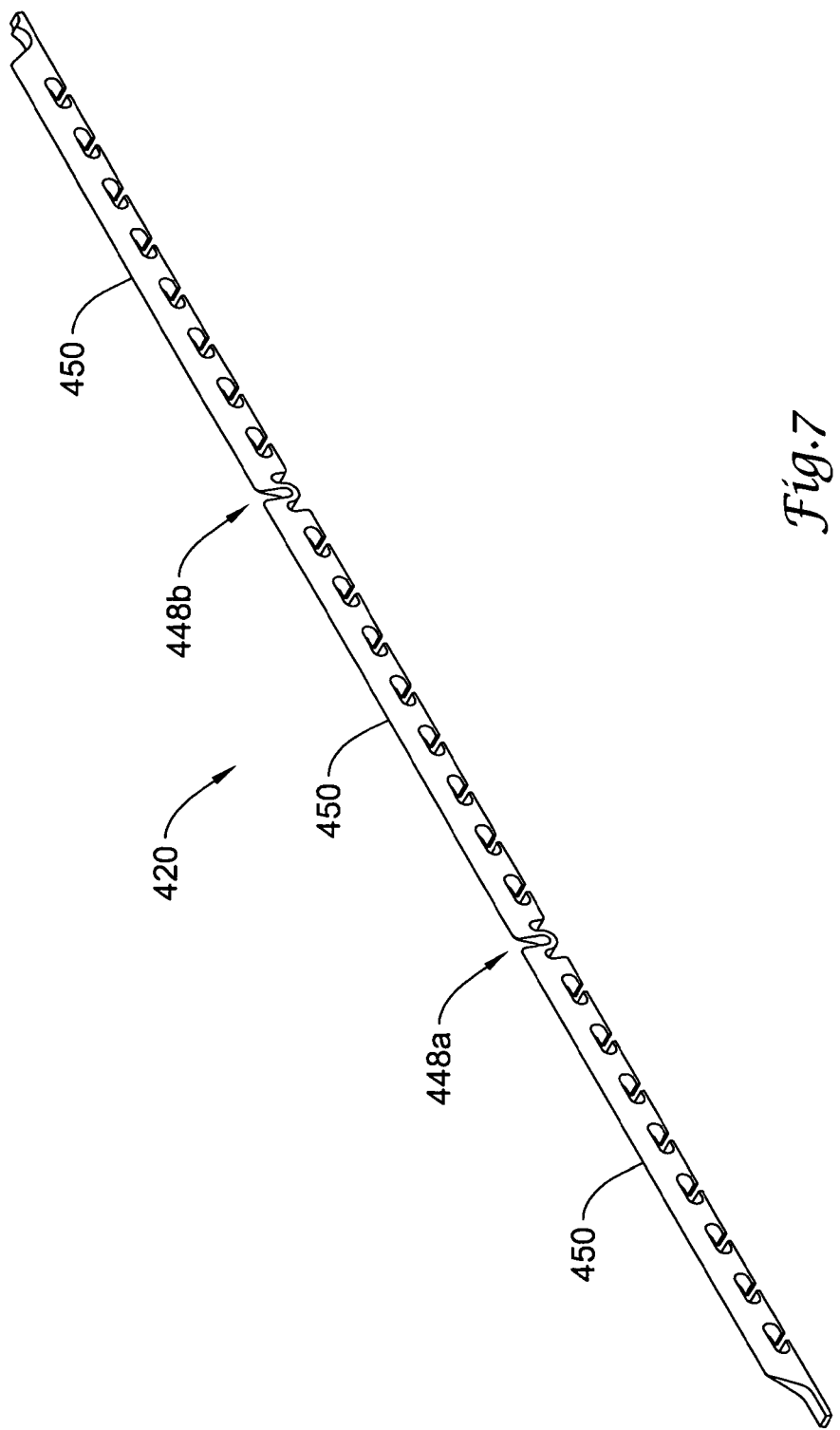
FIG. 7 is a perspective view of another example cutting member.

As the length of cutting member 320 (or other cutting member disclosed herein) changes, the number and position of slots 348 may vary. For example, the length of any of the cutting members disclosed herein may range from about 4 millimeters to about 20 millimeter or so. Generally, as the length increases, the number of slots that may be desirable increases. Accordingly, relatively short cutting members (e.g., about 4-7 millimeters or so) may not have any slots. Slightly longer cutting members (e.g., about 7-14 millimeters or so) may include one slot similar to slot 348 in cutting member 320. Even longer cutting members (e.g., about 12 millimeters or longer) may include more than one slot. For example, FIG. 7 illustrates cutting member 420 that has two slots 448a/b disposed along cutting edge 450. Of course, a number of addition embodiments of cutting members are contemplated that have a variety of lengths and numbers of slots.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed:

1. A cutting balloon catheter, comprising:
   an elongate catheter shaft;
   an inflatable balloon coupled to the catheter shaft proximate a distal end of the catheter shaft;
   a flexible joining member mounted on the balloon; and
   a cutting member having a base portion embedded within the flexible joining member, the cutting member constructed of a single continuous piece of material forming a first cutting edge portion, a second cutting edge portion, and a flexible bridge spanning a gap between the first cutting edge portion and the second cutting edge portion ;
   wherein the flexible bridge is embedded within the flexible joining member.

2. The cutting balloon catheter of claim 1, wherein the gap extends to an upper extent of the cutting member.

3. The cutting balloon catheter of claim 2, wherein an upper extent of the first cutting edge portion includes a first sharpened cutting edge and an upper extent of the second cutting edge portion includes a second sharpened cutting edge.

4. The cutting balloon catheter of claim 3, wherein the gap spaces apart the first and second sharpened cutting edges.

5. The cutting balloon catheter of claim 1, wherein a portion of the flexible joining member is disposed in the gap above the flexible bridge.

6. The cutting balloon catheter of claim 1, wherein the flexible joining member includes a polymeric material.

7. The cutting balloon catheter of claim 1, wherein the base portion includes alternating tabs and holes.

8. The cutting balloon catheter of claim 7, wherein the alternating tabs and holes provide interlocking engagement with the flexible joining member.

9. The cutting balloon catheter of claim 8, wherein the holes are filled with material of the flexible joining member.

10. The cutting balloon catheter of claim 1, wherein the elongate catheter shaft includes an inner tubular member and an outer tubular member surrounding the inner tubular member.

11. The cutting balloon catheter of claim 10, wherein a proximal waist of the inflatable balloon is affixed to the outer tubular member and a distal waist of the inflatable balloon is affixed to the inner tubular member.

12. A cutting balloon catheter, comprising:
    an elongate catheter shaft;
    an inflatable balloon coupled to the catheter shaft proximate a distal end of the catheter shaft;
    a flexible joining member mounted on the balloon; and
    a cutting member constructed of a single continuous piece of material forming a first cutting edge portion, a second cutting edge portion and a flexible bridge, the first cutting edge portion having a first base portion embedded within the flexible joining member and a first cutting edge at an upper extent of the first cutting edge portion, the second cutting edge portion having a second base portion embedded within the flexible joining member and a second cutting edge at an upper extent of the second cutting edge portion, and the flexible bridge spanning a gap between the first cutting edge and the second cutting edge such that the first cutting edge is discontinuous from the second cutting edge;
    wherein the flexible bridge is embedded within the flexible joining member.

13. The cutting balloon catheter of claim 12, wherein a portion of the flexible joining member is disposed in the gap above the flexible bridge.

14. The cutting balloon catheter of claim 12, wherein the flexible joining member includes a polymeric material.

15. The cutting balloon catheter of claim 12, wherein the first and second base portions include alternating tabs and holes embedded in the flexible joining member.

16. The cutting balloon catheter of claim 15, wherein the alternating tabs and holes provide interlocking engagement with the flexible joining member.

17. The cutting balloon catheter of claim 15, wherein the holes are filled with material of the flexible joining member.

18. The cutting balloon catheter of claim 12, wherein the elongate catheter shaft includes an inner tubular member and an outer tubular member surrounding the inner tubular member.

19. The cutting balloon catheter of claim 18, wherein a proximal waist of the inflatable balloon is affixed to the outer tubular member and a distal waist of the inflatable balloon is affixed to the inner tubular member.

* * * * *